United States Patent [19]

Peterson et al.

[11] Patent Number: 4,476,870
[45] Date of Patent: Oct. 16, 1984

[54] FIBER OPTIC $P_{O_2}$ PROBE

[75] Inventors: John I. Peterson; Raphael V. Fitzgerald, both of Falls Church, Va.

[73] Assignee: The United States of America as represented by the Department of Health and Human Services, Washington, D.C.

[21] Appl. No.: 396,055

[22] Filed: Jul. 7, 1982

Related U.S. Application Data

[63] Continuation-in-part of Ser. No. 363,425, Mar. 30, 1982, abandoned.

[51] Int. Cl.³ .............................................. A61B 5/00
[52] U.S. Cl. ................................... 128/634; 128/665; 128/666; 250/458.1; 356/41
[58] Field of Search ............... 128/633–635, 128/664, 665, 666; 356/39–41; 250/458.1, 459.1

[56] References Cited

U.S. PATENT DOCUMENTS

| | | | |
|---|---|---|---|
| 3,612,866 | 10/1971 | Stevens | 250/483.1 |
| 4,003,707 | 1/1977 | Lubbers et al. | 128/634 |
| 4,200,110 | 4/1980 | Peterson et al. | 128/634 |
| 4,215,940 | 8/1980 | Lubbers et al. | 356/41 X |
| 4,269,516 | 5/1981 | Lubbers et al. | 356/39 X |
| 4,306,877 | 12/1981 | Lubbers | 356/39 X |

OTHER PUBLICATIONS

Peterson et al., Rev. Sci. Instrum., May 1980, pp. 670–671.
Peterson et al., Anal. Chem., vol. 52, No. 6, May 1980, pp. 864–869.

Primary Examiner—Kyle L. Howell
Assistant Examiner—J. C. Hanley
Attorney, Agent, or Firm—Browdy and Neimark

[57] ABSTRACT

A fiber optic probe to be implanted in human body tissue for physiologic studies involving measurement and monitoring of the partial pressure of gaseous oxygen in the blood stream, which is coursing through a particular blood vessel in the body. The use of the probe is based on the principle of dye fluorescence oxygen quenching. Structurally the probe comprises two 150-micrometer strands of plastic optical fiber ending in a section of porous polymer tubing serving as a jacket or envelope for the fibers. The tubing is packed with a suitable fluorescent light-excitable dye placed on a porous adsorptive particulate polymeric support. The tubing or jacket is usually made of a hydrophobic, gas-permeable commercial material, known as Celgard, but other suitable hydrophobic gas-permeable material could be used for such structure. The fiber optic probe of the invention is of very small size and flexible so that it can easily be threaded through small blood vessels which are located in a variety of tissues of the body.

14 Claims, 7 Drawing Figures

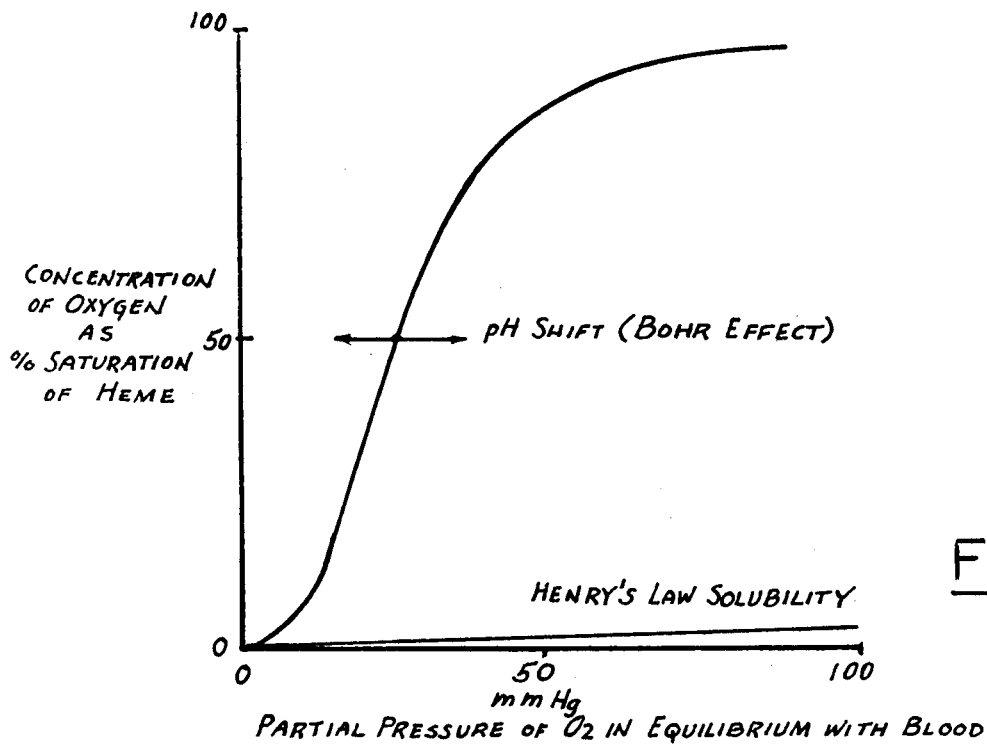
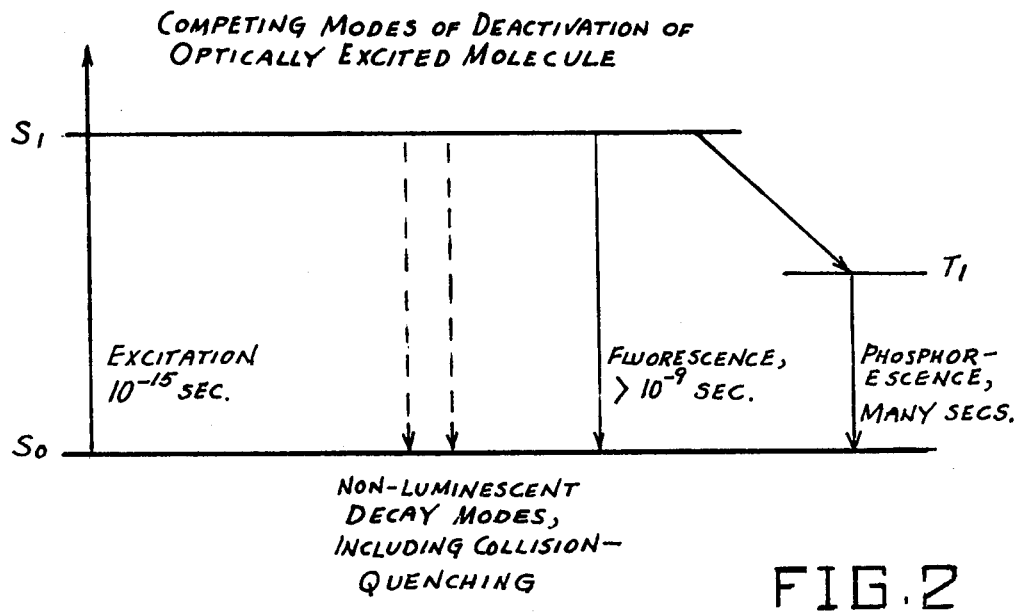

IDEALLY, P' SHOULD BE OF THE ORDER OF $P_{O_2}$ TO BE MEASURED
TO COMPROMISE SENSITIVITY AND BRIGHTNESS

SENSITIVITY $S = \dfrac{-d(\%I)}{d(\%P_{O_2})} = \dfrac{P_{O_2}}{P' + P_{O_2}}$

BRIGHTNESS $B = \dfrac{I}{I_o} = \dfrac{P'}{P' + P_{O_2}}$

INTENSITY – PRESSURE RELATION

THEORETICAL
$\dfrac{I_o}{I} = 1 + \dfrac{P_{O_2}}{P'}$
STERN-VOLMER

TYPICAL DATA CURVE
$\left(\dfrac{I_o}{I}\right)^m = 1 + \dfrac{P_{O_2}}{P'}$

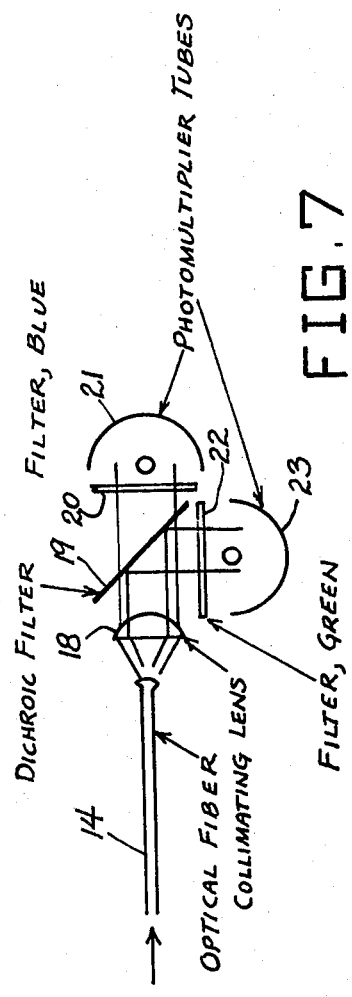
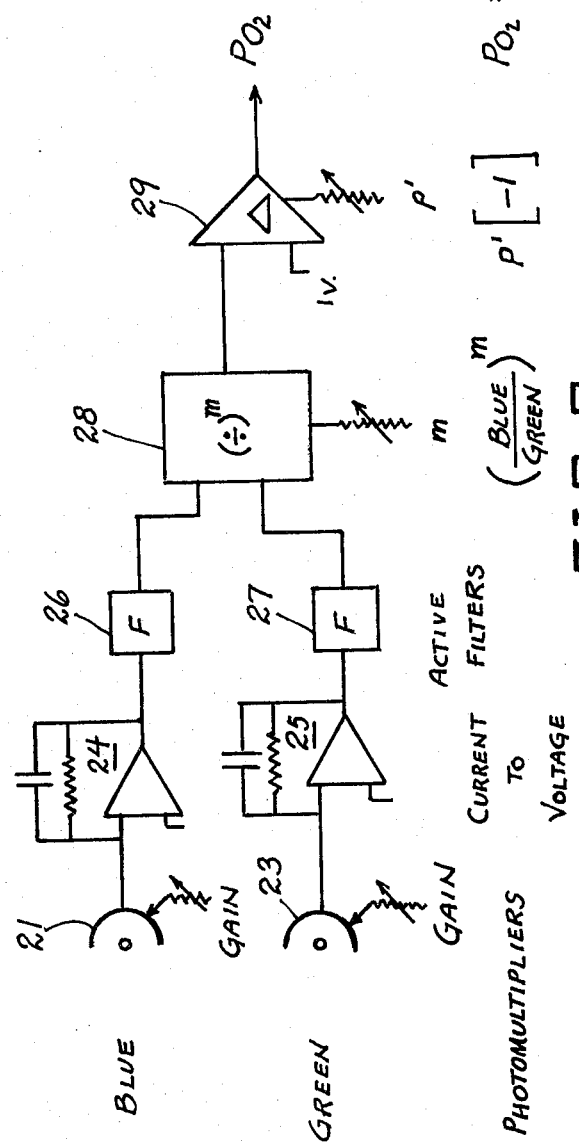

FIBER OPTIC P$_{O_2}$ PROBE

This application is a continuation-in-part of our previously filed application Ser. No. 363,425, now abandoned, filed Mar. 30, 1982, entitled "Fiber Optic P$_{O_2}$ Probe", the contents of which are incorporated by reference.

FIELD OF THE INVENTION

The present invention relates to measurement of oxygen partial pressure, and more particularly to a fiber optic probe device for implantation to measure oxygen partial pressure in the blood or tissue.

BACKGROUND OF THE INVENTION

Physiologic oxygen measurement is important for many reasons, as follows:

The transfer function (FIG. 1) is the fundamental determinant of oxygen transport and distribution.

Adsorption of O$_2$ by heme is the most widely used mechanism of oxygen storage and transport throughout the animal kingdom.

The corresponding protein change (globin) embedding the heme controls its adsorptive characteristics, and determines the shape of the transfer function, thus suiting the heme to the needs of a particular species.

The globin chain also is part of a control loop to adjust the curve to biochemical signals, most significantly pH, 2,3-di-phosphoglycerate and CO$_2$.

In people, approximately 200 genetic variants of hemoglobin are known; most are innocuous, some are pathologically severe because of alteration of the transfer function (sickle cell disease, etc.).

Direct measurement of P$_{O2}$ is therefore necessary to observe the oxygen transport behavior in an individual in any physiologic investigation.

Moreover, adequate tissue oxygenation is one of the most important short-range concerns in a variety of surgical and intensive care situations, requiring either quick response sampling or continuous monitoring of P$_{O2}$ levels.

A number of techniques and systems are known, but none of these is entirely suitable. For example:

The Clark electrode (membrane-diffusion, amperometric) does not lend itself to small size.

The diffusion dependence is subject to calibration and drift problems.

A strictly potentiometric (redox) electrode has specificity difficulties.

Haase, U.S. Pat. No. 4,201,222 discloses an optical catheter, including a fiber optic bundle, adapted to be inserted into a blood vessel of a living body for measuring the partial pressure of oxygen gas in the blood stream. The catheter comprises a semipermeable wall member for excluding the entry therethrough of blood liquid while permitting passage of blood gases. The intensity of a reflected visible light beam entering the optical fiber bundle, when compared to the intensity of the incident beam, is said to accurately correspond to the partial pressure of the oxygen gas in the bloodstream.

Mori, U.S. Pat. No. 3,814,081 discloses an optical catheter for measuring the percentage content of oxygen saturating the blood stream of a living animal body. An illuminating fiber optic system and a light receiving system are arranged closely adjacent to one another. The tip of the catheter is inserted into a blood-carrying organ of the animal body. The degree of oxygen saturation is measured by a light absorption spectroscopic detemination of light waves which are reflected from the blood stream and received by an optical fiber bundle.

Ostrowski et al. U.S. Pat. No. 3,807,390 disclose a fiber optic catheter for monitoring blood oxygen saturation in a human blood stream, in vivo, by insertion of the catheter tip into the cardiovascular system of the living body.

Willis et al. U.S. Pat. No. 4,033,330 is of general interest in showing a transcutaneous optical pH measuring device for determining blood pH or carbon dioxide concentration in the blood. Fostick U.S. Pat. No. 4,041,932 is likewise of general interest in teaching an apparatus used to measure and monitor the concentration and partial pressure of gases, such as oxygen and carbon dioxide in arterial blood vessels, and the pH of the blood during various time periods.

The P$_{O2}$ electrode literature is enormous, but there is still not a suitable electrode available.

Oxygen measurement by luminescence quenching has also been suggested. The idea originated in the 1930's, but has had relatively little use, although oxygen quenching of fluorescence is widely recognized as a nuisance. Stevens U.S. Pat. No. 3,612,866 discloses an apparatus for measuring the oxygen content concentration of liquids or gases based on the molecular luminescence quenching effect of gaseous oxygen on aromatic molecules, derivatives of such aromatics and aliphatic ketones.

Other applications of luminescence quenching for oxygen determination include:

1. Original observation of effect—dyes adsorbed on silica gel: H. Kautsky and A. Hirsch in early 1930's, e.g. H. Kautsky and A. Hirsch, Z. fur anorg. u. allgem. Chemie 222, 126–34, 1935.

2. Measurement of O$_2$ produced by illumination of algae: M. Pollack, P. Pringsheim and D. Terwood, J. Chem. Phys., 12, 295–9, 1944.

3. Catalog of oxygen quenching sensitivities of organic molecules of scintillation interest: I. B. Berlman, "Handbook of Fluorescence Spectra of Aromatic Molecules", Academic Press, 1965.

4. O$_2$ measured down to $10^{-5}$ torr with acriflavin on acrylic sheet: Gy. Orban, Zs. Szentirmay and J. Patko, Proc. of the Intl. Conf. on Luminescence, 1966, v. 1, 611–3, 1968.

5. Diffusion coefficient of O$_2$ in acrylics measured by observing the phosphorescence of rods: G. Shaw, Trans. Faraday Soc. 63, 2181–9, 1967.

6. O$_2$ permeability of acrylic films measured by quench rate vs. P$_{O2}$ : P. F. Jones, Polymer Letters 6, 487–91, 1968.

7. P$_{O2}$ measuring instrument based on fluoranthene adsorbed on plastic films and porous vycor: I. Bergman, Nature 218, 396, 1968.

8. Pyrenebutyric acid used as probe for measuring intracellular O$_2$: J. A. Knopp and I. A. Longmuir, Biochimica et Biophysica Acta, 279, 393–7, 1972.

9. Physiological P$_{O_2}$ measurement using DMF solutions of pyrenebutyric acid in various membrane-enclosed forms, D. W. Lubbers and N. Opitz, Z. Naturf. 30c, 532–3, 1975.

SUMMARY OF THE INVENTION

It is accordingly an object of the invention to overcome the defects of the prior art, such as above described.

Another object of the invention is to provide for improved $P_{O2}$ in vivo measurement.

A further object of the invention is to provide for an improved $P_{O2}$ measurement device, particularly one based on oxygen measurement using luminescence quenching and including a fiber optic probe.

A still further object of the invention is to provide an improved $P_{O2}$ measurement device employing luminescence quenching as its operational principle and utilizing a fiber optic probe in combination with a relatively simple optical system in association with photomultiplier tubes and an electronic computing circuit driven by said photomultiplier tubes and arranged to provide a direct analog computation of $P_{O2}$ based on said luminescence quenching as detected by said optical system.

A typical fiber optic probe for measuring oxygen partial pressure according to the present invention, based on the principle of fluorescence quenching, comprises two 150-micrometer strands of plastic optical fiber ending in a section of porous polymer tubing about 5 mm long and 0.6 mm in diameter. The tubing is packed with a dye on an adsorptive particulate support. The general construction is similar to a physiological pH probe which has previously been described in the Peterson et al. U.S. Pat. No. 4,200,110.

Development of the probe of the present invention required the solution of three major problems not encountered before in the application of the above-mentioned quenching principle:

1. A dye had to be found with the combined properties of suitable oxygen quench sensitivity (long activated state lifetime), fluorescence excitation by visible light, and resistance to fading. Plastic optical fibers which transmit light sufficiently at wavelengths shorter than 450 nm are not available. Ultraviolet transmitting inorganic fibers are not desirable for this application because of their brittleness.

2. A suitable hydrophobic, high-oxygen-permeability envelope was necessary.

3. An adsorptive support was required which activated the dye without sensitivity to humidity. The traditional silica dye support is not suitable for use in an aqueous medium.

The probe device of the present invention is intended to provide a small-size, low-cost probe suitable for tissue and blood vessel implantation through a hypodermic needle.

Fiber optic probes have substantial advantages, including the following:

a. Very small size is possible, such as less than 0.5 mm θ.

b. They are flexible, so that they can be threaded through small blood vessels or can be located in a variety of tissues.

c. They are low in cost, disposable, and easy to fabricate.

d. They introduce no electrical hazard.

e. They are suitable for equilibrium measurement, rather than dynamic.

The selection of luminescence quenching as the mechanism for oxygen measurement was based on the following factors:

1. A reversible indicator is needed for a $P_{O2}$ probe. A reversible colorimetric (absorbance) indicator for oxygen is not available. The transition metal complex oxygen absorbers do not have the required stability. 2. Aromatic molecules form charge-transfer complexes with oxygen upon activation by light absorption. This provides a mechanism for deactivation of the fluorescent state which is specific for oxygen. A high energy of activation of the molecule, sufficient to achieve formation of activated oxygen by collision transfer, is not needed, i.e., the quenching phenomenon can be observed with visible light activation of luminescence.

Fluorescence (and phosphorescence) quenching is the result of a non-luminescent decay mode competing with the luminescent decay of an activated molecule, thereby decreasing the mean lifetime of the activated state and decreasing the luminous intensity (see FIG. 2).

With constant illumination, the rate of decay of the excited state is the sum of the rates of the varoius decay modes; the collision decay rate is proportional to the activated state mean lifetime (approximately, the fluorescence lifetime) and the collision rate, which is in turn proportional to the pressure of the quench gas. These competing decay rates result in the Stern-Volmer relation for intensity I and pressure $P_{O2}$ of oxygen:

$$I_o/I = 1 + P_{O2}/P'$$

(O. Stern and M. Volmer, Physikalische Zeitschrift 20, 183–8, 1919), where $I_o$ is the intensity without quenching, and $P^1$ is a constant, the pressure at half-quench. The constant includes a proportionality of corresponding quench to mean fluorescence lifetime, so the same expression can be written in terms of observed luminescence lifetimes, $T_o$ and T:

$$T_o/T = 1 + P_{O2}/P'$$

Good sensitivity to quenching requires a long mean lifetime of the excited state. Phosphorescence, with a very long lifetime (seconds), is very sensitive to quenching, but is weak in intensity. Fluorescence is less sensitive to quenching, but has a high brightness (high quantum efficiency). P' should be of the order of the pressure to be measured to best compromise brightness and sensitivity (see FIG. 3).

BRIEF DESCRIPTION OF THE DRAWINGS

Further objects and advantages of the invention will become apparent from the following description and claims, and from the accompanying drawings, wherein:

FIG. 1 is a graph showing the classic concentration vs. pressure relationship of oxygen in human blood.

FIG. 2 is a schematic representation of competing modes of deactivation of an optically excited molecule.

FIGS. 6 and 7 respectively show schematically the optical system and the electronic computing system of a simple analog instrument employing testing probes according to the present invention.

DETAILED DESCRIPTION OF A PREFERRED EMBODIMENT

Figure 4:
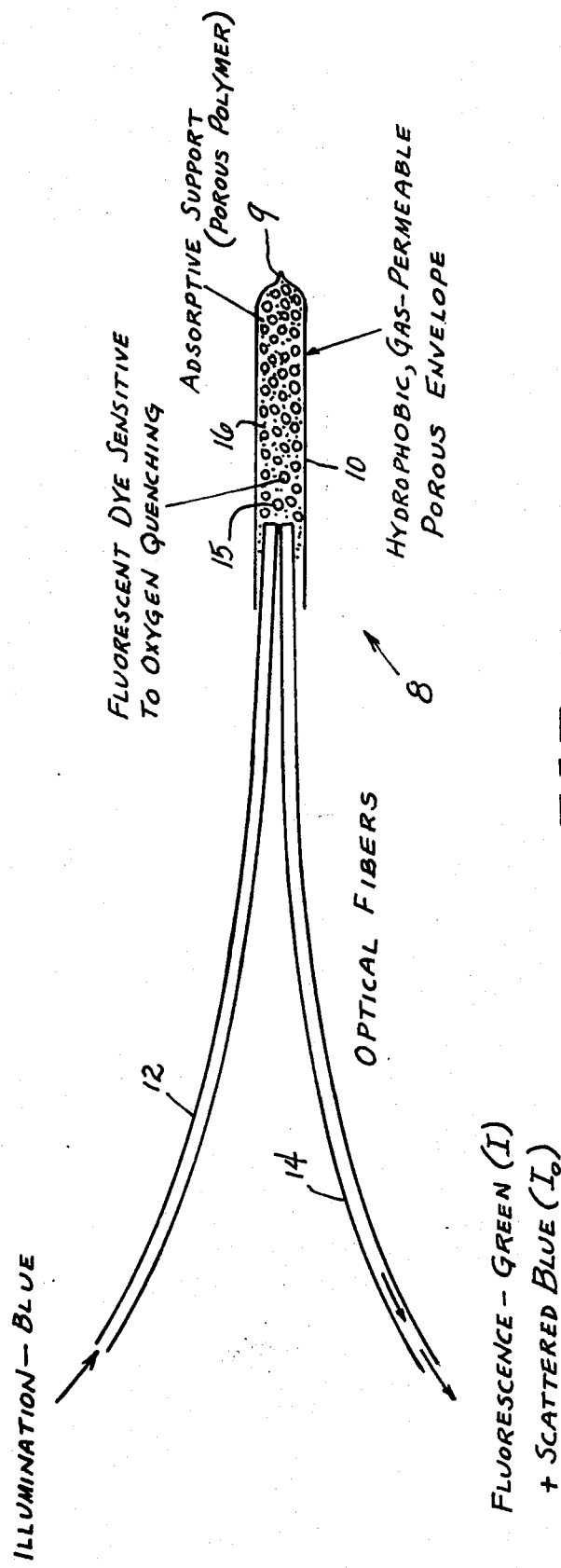
FIG. 4 is a diagrammatic view of an embodiment of a $P_{O2}$ probe in accordance with the present invention.

Referring to the drawings, and more particularly to FIG. 4, a $P_{O2}$ probe according to the present invention is generally designated at 8. The $P_{O2}$ probe 8 is modelled after the pH probe previously developed by us (see Peterson et al., U.S. Pat No. 4,200,110). In the $P_{O2}$ probe 8, the dye 15, on an adsorbent support 16, is contained inside a section of tubing 10 of porous polyethylene, providing rapid equilibration with the surrounding oxygen and isolating the dye packing 16 from contamination. The tubing 10 is closed at one end, providing an axial tapered closure tip 9. A pair of flexible plastic optical fibers 12 and 14, for example, 150-micrometer strands of plastic optical fiber, are suitably secured in the other end of the tubing 10, with their ends optically exposed to the dye 15 in the packing 16. The tubing 10 may comprise a section of porous polymer tubing about 5 mm long and 0.6 mm in diameter.

Blue light illumination passes down one optical fiber 12 to excite the dye 15 to fluorescence. The green fluorescent light, along with scattered blue light, enters the other fiber 14 and passes to a measuring instrument (see FIGS. 6 and 7). The blue light intensity $I_o$ is used as the reference for optical compensation, and the green light intensity I is a measure of the oxygen quenching.

Figure 3:
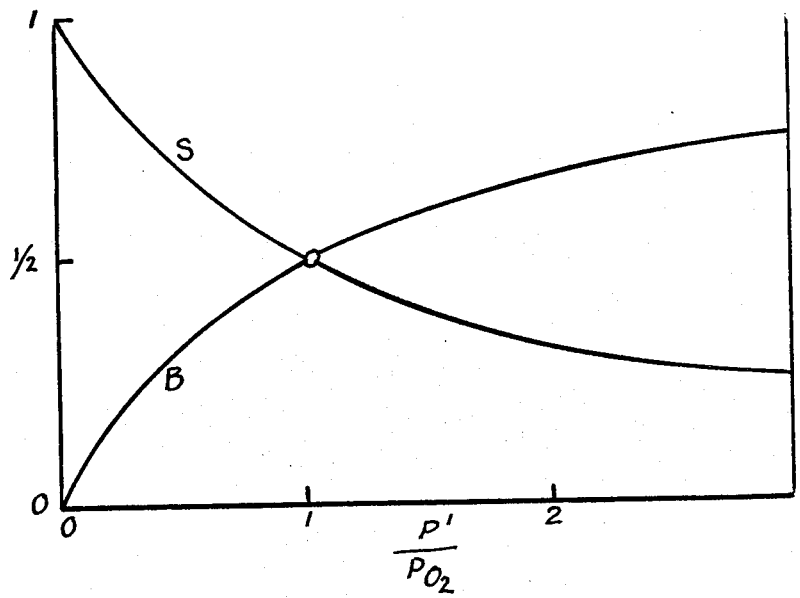
FIG. 3 is a schematic representation showing the relationship between P' and $P_{O2}$.
Figure 5:
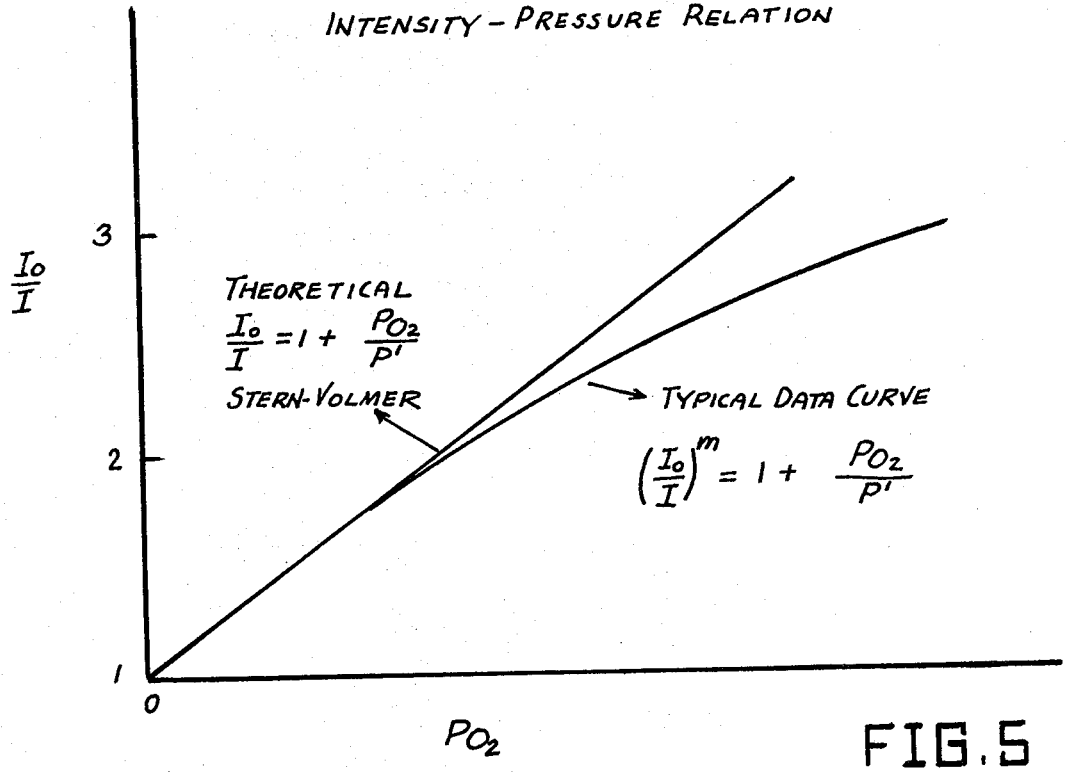
FIG. 5 is a graph comparing theoretical Stern-Volmer data with typically observed data according to the invention.

The Stern-Volmer relation provides a linear quantitative basis for measuring $P_{O2}$ by quenching (see FIG. 5). A curved relation is commonly observed (the literature with Stern-Volmer plotted data is large) and an exponent is often attached to the oxygen pressure to fit the data to the equation.

A theoretical interpretation of the exponential relation is difficult to understand; curved data can be equally well fitted by an offset constant on the intensity measurements, which can be explained as instrumental background or non-quenchable luminescence. For instrumental design purposes, however, using either an exponent m on the intensity ratio or an exponent n on the bracketed difference is more practical:

$$P_{O2} = P'\left[\left(\frac{I_{blue}}{I_{green}}\right)^m - 1\right]^n$$

A simple analog instrument was constructed (see FIGS. 6 and 7) for evaluation of the probes. Measurement of $P_{O2}$ to the nearest $I_{mmHg}\, P_{O2}$ requires better than 0.1% intensity measurement error. Instrumentally, the limiting factor is light source stability.

As noted above, there are three features of the above-described system which need to be properly selected, namely, the dye 15, the dye support 16 and the envelope 10.

A suitable dye 15 has the following characteristics:

a. It must be capable of excitation by and generation of visible wavelengths which can be transmitted by plastic optical fibers of a type which is unbreakable when subjected to sharp bends, is highly flexible, and which can be formed to provide easy optical coupling, such as with flared ends.

b. It must be stable to light and have adequate resistance to aging.

c. It must be non-toxic.

d. It must have sufficient oxygen quenching sensitivity (long mean lifetime of the excited state) as needed to attain measurement to the nearest 1 $mm_{Hg}\, P_{O2}$.

There is a problem in the selection of the dye 15 in that many UV-excited dyes have a high quench sensitivity (benzene has one of the highest), but the requirements of visible light excitation makes it much more difficult to find a dye which will meet the requirement. A suitable dye is perylene dibutyrate. Another suitable dye is Pylam Products LX7878. Less suitable, but usable dyes are Terasil Brilliant Flavine 8GFF; Nylosan Brilliant Flavine; Acridine Yellow; Brilliant Sulfaflavine; 2,7-dichloro fluorescein; Acridine Orange; Coumarin 34; Coumarin 6; sodium fluorescein (uuranine), and some rhodamines. Others have appeared in the literature references given herein.

With regard to a suitable support 16, the quenching effect was classically observed on silica gel, and high sensitivity is achieved on this support. A high-permeability support is necessary to expose the individual dye molecules to oxygen collision. A solution of the dye in liquids or solids is insensitive because of the low oxygen permeability of such materials.

The problem with inorganic adsorbents is that the quenching is humidity-sensitive; quenching and/or fluorescence is destroyed at 100% humidity, the condition of physiologic measurement.

Organic adsorbents, such as porous polymers, avoid the humidity problem, with a sacrifice of quench sensitivity and these polymers, determinable by routine testing in view of this disclosure, are desirably selected. A porous polymer, Rohm & Haas "Amberlite XAD4", a non-ionic hydrophobic polymer, is the preferred support 16. Examples of others are Gas Chrom Q, Amberlite XAD2, XAD8; Dow XFS4022; Johns-Manville Chromosorb, Nos. 101, 102, 103, 104, 105, 106, 107, 108; Waters Porapak Nos. N, P, PS, Q, R, S, QS, T; Hamilton Co. PRP-1.

In the illustrated embodiment of the $P_{O2}$ probe 8, a liquid-water-impermeable container of high oxygen permeability is required for the permeable envelope 10. Porous polypropylene sheet Celanese "Celgard", heat-sealed into tubing, has been found to be suitable.

The described embodiment works in aqueous media as well as in a gaseous system, and behaves satisfactorily in test animals.

The combination of the use of luminescence quenching for oxygen determination, together with fiber optics is believed to be novel and highly advantageous. As noted above, the important features of the invention include the use of a porous polymer support, proper selection of dye, and the use of a porous jacket or envelope. The use of a porous polymer as the dye support 16 is essential for the best performance. As above mentioned, a suitable jacket 10 may be formed of Celgard, although other porous materials can be used.

Variations are possible. Thus, there are alternate ways of making the probe, e.g., a single fiber, rather than two fibers, could be used, with appropriate instrumentation modification, to reduce probe size.

In the typical optical system of FIG. 7, the optical output of fiber 14 is transmitted through a collimating lens 18 to a 45°-inclined dichroic filter 19. The transmitted light component passes through a blue filter 20 to a first photomultiplier tube 21. The reflected light component passes through a green filter 22 to a second photomultiplier tube 23. As shown in FIG. 6, the output currents from the photomultiplier tubes 21 and 23 are fed to respective current-to-voltage converter circuits 24, 25, and the resultant voltage signals are passed through respective active filters 26, 27 to the inputs of divider circuit 28 provided with means to apply an exponent m to the quotient ($I_{blue}$ divided by $I_{green}$, as given above). The $P_{O_2}$ analog value is then computed by feeding the output of circuit 28 to a final computing circuit 29 which subtracts the quantity 1 from its input signal and applies the coefficient P', as indicated in FIG. 6.

It will be obvious to those skilled in the art that various changes may be made without departing from the scope of the invention and that the invention is not to be considered limited to what is shown in the drawings and described in the specification.

What is claimed is:

1. A probe for determining $P_{O_2}$ in the blood or tissue of a living animal, comprising: an oxygen-porous jacket of a size sufficiently small to be passed into a blood vessel; a porous dye support carried within said jacket, said dye support and said jacket having sufficiently high permeability to permit the exposure of individual dye molecules carried thereby to oxygen collision; a non-toxic luminescent dye carried by said porous dye support, said dye being excitable by visible light, having and sufficiently great stability to aging to permit storage without substantial change of dye characteristics, and being oxygen quenching-sensitive; and fiber optic means to pass excitation light to said dye within said jacket and collect luminescence therefrom.

2. A probe according to claim 1, wherein said dye is perylene dibutyrate.

3. A probe according to claim 1 or claim 2, wherein said porous dye support is a porous organic polymer.

4. A probe according to claim 1, and wherein said porous dye support comprises silica gel.

5. A probe according to claim 1, and wherein said porous dye support comprises a porous adsorptive particulate polymeric material.

6. A probe according to claim 1, and wherein said porous dye support comprises Amberlite XAD4.

7. A probe according to claim 1, and wherein said oxygen-porous jacket comprises a tubular envelope of porous material.

8. A probe according to claim 7, and wherein said tubular envelope is formed of Celgard.

9. A probe according to claim 1, and wherein said oxygen-porous jacket comprises porous polypropylene sheet material heat-sealed into tubing, closed at one end and provided at said closed end with a tapered closure tip.

10. A probe according to claim 1, and wherein said fiber optic means comprises at least one strand of transparent plastic fiber with one end extending into said jacket and being optically exposed to said dye.

11. A probe according to claim 1, and wherein said fiber optic means comprises two strands of transparent flexible plastic fiber with ends extending into said jacket and being optically exposed to said dye.

12. A probe according to claim 1, and wherein said fiber optic means includes a strand of transparent plastic fiber with one end extending into said jacket and being optically exposed to said dye, optical beam-splitting means optically exposed to the other end of said plastic fiber and forming two spaced optical beams from the light transmitted through the fiber, respective photoelectric signal generating means in the paths of said two optical beams, and $P_{O_2}$ computing circuit means connected to the outputs of said photoelectric signal generating means.

13. A probe according to claim 12, and respective different-color filter means optically interposed in the paths of the two optical beams between the beam-splitting means and the photoelectric signal generating means.

14. A probe according to claim 13, and wherein one color filter means passes only light corresponding to the luminescence wavelength of the dye, and the other color filter means passes light only of a color corresponding to that of scattered incident light to which the dye is exposed and which is reflected from the dye.

* * * * *